United States Patent [19]

Meldrum et al.

[11] Patent Number: 4,877,533

[45] Date of Patent: Oct. 31, 1989

[54] SEPARATION OF WATER FROM ORGANIC FLUIDS

[75] Inventors: Ian G. Meldrum, Leatherhead; Timothy d. Naylor, Woking, both of England

[73] Assignee: British Petroleum Company p.l.c., London, England

[21] Appl. No.: 140,908

[22] Filed: Dec. 29, 1987

Related U.S. Application Data

[63] Continuation of Ser. No. 841,531, filed as PCT GB85/00331 on Jul. 25, 1985, Published as WO86/00819 on Feb. 13, 1986, abandoned.

[30] Foreign Application Priority Data

Jul. 27, 1984 [GB] United Kingdom ............... 8419174

[51] Int. Cl.$^4$ ............................................. B01D 13/00
[52] U.S. Cl. ........................... 210/640; 159/DIG. 27; 203/19; 203/DIG. 13
[58] Field of Search .......................... 210/640; 55/16; 159/DIG. 27; 203/19, DIG. 13

[56] References Cited

U.S. PATENT DOCUMENTS 3,950,247  4/1976  Chiang et al. ...................... 210/640

FOREIGN PATENT DOCUMENTS 0146655  7/1985  European Pat. Off. .
2227037  11/1974  France .
1351188  4/1974  United Kingdom .

Primary Examiner—Ivars Cintins
Attorney, Agent, or Firm—Morgan & Finnegan

[57] ABSTRACT

Water is separated from a less hydrophilic fluid by contacting the mixture with one face of a membrane having an active layer which consists essentially only of polymers of an unsaturated organic acid with a ratio of carbon atoms to acid groups (not counting any carbon atoms in the acid groups) of not more than six. Water is removed as a vapor from the other side of the membrane.

17 Claims, No Drawings

SEPARATION OF WATER FROM ORGANIC FLUIDS

This is a continuation of co-pending application Ser. No. 841,531, filed as PCT GB85/00331 on Jul. 25, 1985, published as WO86/00819 on Feb. 13, 1986, now abandoned.

The present invention relates to the separation of water from fluids by the pervaporation process. In the pervaporation process a mixture of fluids is maintained in contact with one side of a suitable membrane. One of the components of the fluid permeates preferentially through the membrane and is removed from the other side as a vapour.

Membranes are used in a variety of processes. Thus membranes are used in the desalination of water by reverse osmosis. Other membrane processes are known involving the separation of ionic species. For this purpose it is known to use membranes containing cations in the treatment iof electrolytes. Thus "Membrane Processes in Industry and Biomedicine", Plenum Press, New York, 1971, edited by M. Bier refers on page 303 to membranes formed from polystyrene sulphonic acid in the sodium form embedded in collodion. These are used for treating electrolytes. The membranes used in processes involving electrolytes are generally porous. There is a reference in the same publication to the use of poly(acrylic) acid on a support to make a composite membrane. There is no suggestion that this should be used in the salt form.

Derwent abstract 28548K/12 discloses a dehydrating agent for removing water from eg ethanol which comprises an alkali metal salt of cross-linked carboxymethyl cellulose. There is no reference in the abstract to the use of membranes and the material appears to be used as a simple absorbing agent.

Derwent abstract 81265S discloses the separation of water from aqueous solutions of organic compounds using a membrane consisting of an organic polymer possessing active anionic groups derived from eg organic acids and also cationic groups. The process involves permeation from one liquid phase to another and is not a pervaporation process.

In Derwent abstract 78357Y/44 a membrane containing cations is disclosed for use in a pervaporation process. The membrane is obtained by copolymerising an olefin with a carboxylic unsaturated compound. The process is used for separating various organic liquids. There is no mention in the abstract of the use of the membrane for separating water from organic fluids having not more than six carbon atoms for every acid group (not counting any carbon atoms in the acid group).

DE 30 37 736 discloses the separation of water from ethanol using pervaporation. The membrane used is a cellulose acetate membrane.

In the separation of water from fluids by pervaporation two characteristics of the membrane are important, in addition to its resistance to attack by the fluid mixture. One of these characteristics is the flux, the amount of material passing through a given area in a given time. The other is the selectivity, namely the proportion of the required component in the total material passing through the membrane. It is particularly desirable for economic reasons to find materials which give high flux rates without impaired selectivity.

According to the present invention the process for separating water from a mixture with a less hydrophilic fluid by bringing the mixture into contact with one side of a membrane and removing water vapour from the other side of the membrane is characterised in that the membrane has an active layer which consists essentially only of polymers of an unsaturated organic acid, the acid having not more than 6 carbon atoms for every acid group (not counting any carbon atoms in the acid groups), and the polymer having at least a substantial proportion of the acid groups in the form of a salt.

By fluids which are less hydrophilic than water we mean fluids which have a lower solubility parameter number as defined in The Polymer Handbook edited by Brandup and Immergut, published by Interscience.

The preferred fluids for use in the process of the present invention are organic fluids. The fluid may be a gas eg hydrocarbon gases in particular methane. The fluid may be a liquid and the process of the present invention is particularly suitable for the removal of water from organic liquids.

The process of the present invention is particularly suitable for separating water from mixtures with alkanols, in particular alkanols having 1 to 5 carbon atoms in the molecule, eg ethanol and isopropanol.

The unsaturated organic acid preferably has not more than four carbon atoms for every acid group (not counting any carbon atoms in the acid group), more preferably not more than three carbon atoms for every acid group. This lower number of carbon atoms are particularly preferred when the acid is a carboxylic group. Thus the unsaturated organic acid may be one having not more than four carbon atoms in the molecule.

Where the acid group is a strong acid eg a sulphur acid group, good results may be obtained with a higher ratio of carbon atoms to acid groups.

The unsaturated acid (apart from the acid group or groups) preferably consists only of carbon hydrogen and oxygen, more preferably of carbon and hydrogen only.

The active layer may be prepared from a single unsaturated acid. Where a mixture is used the values quoted above for numbers of carbon atoms are average values for the mixture.

The unsaturated organic acid may be a sulphur acid eg sulphonate or sulphate or a phosphorus acid but is preferably a carboxylic acid. Thus the active layer may be poly(acrylic acid) or poly(maleic acid).

The membrane is used with at least a substantial proportion preferably at least 50%, more preferably at least 75%, most preferably substantially 100% of the acid groups in the salt form. The cation is preferably a metal cation eg an alkali metal or alkaline earth metal. Alkali metal salts are preferred. The preferred alkali metal cation is caesium.

The molecular weight and/or degree of cross-linking of the polymer must of course be sufficient to prevent dissolution of the polymer by the organic liquid, as will be apparent to any person skilled in pervaporation. Thus the molecular weight is preferably at least 1000, more preferably at least 20000 (wt. average). Any cross-linking agents used should be present in minor amounts only e.g. less than 10% preferably less than 1% by weight.

The active layer used in pervaporation processes is a dense non-porous layer, and this distinguishes the membranes used in the present invention from some membranes used in treating electrolytes. The active layer however is preferably part of a multi-layer membrane containing a microporous support layer. Such multi-layer membranes are well known to those skilled in pervaporation. Pervaporation techniques are well known and methods for using the membrane will be readily apparent to skilled persons.

The removal of water is preferably carried out at slightly elevated temperatures eg 45° to 90° C.

The process of the present invention requires that a substantial proportion of the acid groups in the polymer should be in the form of the salt. It will be readily understood by the skilled person that the process cannot be applied to mixtures which are sufficiently acid to convert the salt to the acid form. The process is preferably applied to akaline or neutral mixtures eg having a pH in the range 7 to 14.

The process of the present invention requires the fluid it is desired to remove from the mixture to diffuse across a non-porous layer. Any cracking of the membrane will adversely affect its performance by allowing material to pass the membrane otherwise than through the non-porous layer. We have found that the choice of cation used in the membrane can affect the susceptibility to cracking and we particularly prefer to use caesium as the cation for this reason.

In addition to, or instead of, selecting a cation giving resistance to cracking it may be possible to incorporate small amounts of a polymer unit derived from a monomer capable of acting as an internal plasticizer giving a copolymer having a low glass transition temperature for example below 100° C.

An example of such a comonomer is methyl acrylate. However as indicated above any such additional components should be present in only minor amounts.

The invention will now be illustrated by reference to the following Example.

EXAMPLE 1

A commercially available poly(acrylic acid) having a molecular weight of 260 000 was dissolved in water to form a 0.5% wt/wt solution. Slightly less than a molar equivalent of sodium carbonate was added to convert the polymer from the acid formed to the sodium salt. By using slightly less than a molar equivalent the presence of unreacted salt was avoided.

The solution was centrifuged at 2,000 rpm for 90 minutes to remove dust and dirt particles. It was then carefully run onto a commercially available ultrafiltration polysulphone membrane. Such membranes are commercially available from Millipore, Sartorius, or De Danske Sukkerfabrikker A.S. The support membrane was selected to be stable at the operating temperatures used.

The water was allowed to evaporate in a dust-free environment over a period of more than 24 hours. The quantity of sodium poly(acrylate) solution used was selected so as to give a coating weight on the support membrane in the range 0.006 to 0.00015 g cm$^{-1}$.

The apparatus used consisted of a stainless steel test cell equiped with a pressure gauge, relief valve, magnetic stirrer and thermometer. The membrane was supported on a porous stainless steel disc and sealed into the test cell with rubber "O" rings. The porous support and membrane divided the cell into two portions, an upper portion which was designed to be filled with liquid and a lower portion which was connected to a vacuum pump by way of a trap cooled with liquid nitrogen, in which any vapour permeating the membrane is collected. The cell was heated and agitated by a combined heater and magnetic stirrer.

The results obtained are set out in Table 1.

TABLE 1

|  | Feed % wt | Permeate % wt | Flux kg · m$^{-2}$ day$^{-1}$ | Selectivity alpha |
|---|---|---|---|---|
| Ethanol | 90 | 0.4 | 12–17 | 2241 |
| Water | 10 | 99.6 |  |  |

Feed Temperature 60° C.

$$\text{alpha} = \frac{(H_2O/\text{ethanol}) \text{ in permeate}}{(H_2O/\text{ethanol}) \text{ in feed}}$$

By way of comparison details of flux and selectivity obtained using a membrane comprising polyvinyl alcohol cross-linked with maleic acid deposited on a polyacrylonitrile polyester support layer are given in Example 1 of DE No. 3 220 570A. For an 80% ethanol, 20% water feed the flux was 0.96 kg m$^{-2}$ day$^{-1}$ and the selectivity was 1400. The other Examples show much lower selectivities.

COMPARATIVE TEST A

This is a comparative test not according to the invention showing the use of a polyvinyl alcohol membrane.

A commercially available poly(vinyl alcohol) having a molecular weight of 125,000 and 89–90% degrees of hydrolysis was dissolved in water to form a 0.5% wt/wt solution.

The solution was centrifuged at 2,000 rpm for 90 minutes to remove dust and dirt particles. It was then carefully run onto a commercially available polysulphone ultrafiltration membrane having a molecular weight cut off of 10,000 such as a (Millipore PTGC ultrafiltration membrane).

The water was allowed to evaporate in a dust-free environment over a period of more than 24 hours. The quantity of poly(vinyl alcohol) solution used was selected so as to give a coating weight of polymer on the support membrane in the range 0.006 to 0.0015 g.cm$^{-2}$.

The membrane was tested as in Example 1.

The results are shown in Table 2.

TABLE 2

|  | Feed % wt | Permeate % wt | Flux kg · m$^{-2}$ day$^{-1}$ | Selectivity |
|---|---|---|---|---|
| Ethanol | 90 | 64.4 | 126 | 4.9 |
| Water | 10 | 35.6 |  |  |

The results show low selectivity of poly(vinyl alcohol).

Comparison with the result from DE No. 3 220 570A (which uses a cross-linked poly(vinyl alcohol) membrane shows that selectivity can be increased but at a very considerable reduction in flux.

EXAMPLE 2

An experiment was carried out as in Example 1 again using a sodium poly(acrylate) membrane but using samples of ethanol/water feeds of different composition. The feed temperature was 60° C. and the pH of the feed was 11.0.

The results are given in Table 3. In this Table the values quoted for feed water concentration are those measured in the test cell at the end of each sample run. As the experiments were performed batchwise and the fluxes were so high the feed concentrations changed significantly during each run. This was particularly the case for samples with more than 5% wt water in the feed.

TABLE 3

| Sample No. | 1 | 2 | 3 | 4 | 5 | 6 | 7 | 8 |
|---|---|---|---|---|---|---|---|---|
| Permeate Water Concentration wt % | 99.8 | 99.4 | 91.1 | 96 | 96 | 83.5 | 87 | 81.6 |
| Total Flux kg·m$^{-2}$·day$^{-1}$ | 12.3 | 3.5 | 3.9 | 2.5 | 1.85 | 1.95 | 1.4 | 1.3 |
| Water Flux kg·m$^{-2}$·day$^{-1}$ | 12.27 | 3.47 | 3.5 | 2.4 | 1.8 | 1.6 | 1.2 | 1.06 |
| Feed Water Concentration wt % | 10 | 6.4 | 6.0 | 5.3 | 4.6 | 4.3 | 3.5 | 3.0 |

EXAMPLES 3 AND 4

Experiments were carried out as in Example 2 but using a potassium (Example 3) and ammonium (Example 4) (polyacrylate) membrane. The membranes were prepared as in Example 1 but using potassium or ammonium carbonate in place of sodium carbonate. The polymer solution was treated with sufficient potassium carbonate to give a pH of 10.5. The support membrane was a commercially available polysulphone ultrafiltration membrane available for De Danske Sukkerfabrikker A.S. under the designation GR40 PP.

The results are given in Tables 4 and 5.

TABLE 4

| Sample No | 1 | 2 | 3 | 4 | 5 | 6 |
|---|---|---|---|---|---|---|
| Permeate Water Concentration wt % | 98.9 | 98.4 | 98.7 | 98.9 | 99.5 | 99.7 |
| Total Flux kg·m$^{-2}$·day$^{-1}$ | 42.7 | 41.22 | 31.4 | 22.1 | 9.3 | 5.1 |
| Feed Water Concentration wt % | 9 | 8 | 7.35 | 6.9 | 4.3 | 4.15 |

TABLE 5

| Sample No | 1 | 2 |
|---|---|---|
| Permeate Water Concentration wt % | 21.1 | 7.8 |
| Total Flux kg·m$^{-2}$·day$^{-1}$ | 26.1 | 10 |
| Feed Water Concentration wt % | 5.5 | 0.78 |
| Selectivity | 8.7 | 4 |

EXAMPLE 5

An experiment was carried out as in Example 2 but using a caesium poly(acrylate) membrane prepared by replacing the sodium carbonate used in Example 2 with caesium carbonate. Slightly less than a molar equivalent was used as in Examples 1 and 2.

The results are given in Table 6.

The results demonstrate that very significantly improved performances are obtained by changing the counter-ion from sodium to caesium.

EXAMPLES 6 AND 7

These experiments show the use of a membrane derived from a polymer of an unsaturated acid other than acrylic acid.

Potassium polyvinyl phosphate (Example 6) and caesium polyvinyl phosphate (Example 7) prepared as follows:

A commercially available sample of polyvinyl phosphate was neutralised with ether potassium or caesium hydroxide until the pH of the polymer solution was 11.0. The solutions were purified and membranes prepared as described in Example 1.

The membrane was tested as in Example 1.

The results are given in Tables 7 and 8.

TABLE 7

| Potassium Polyvinyl Phosphate - Ethanol/Water | | | | | |
|---|---|---|---|---|---|
| Sample No | 1 | 2 | 3 | 4 | 5 |
| Permeate Water Concentration wt % | 98 | 96.6 | 96.6 | 91 | 97 |
| Total Flux kg·m$^{-2}$·day$^{-1}$ | 3.7 | 4.4 | 4.3 | 3.4 | 27 |
| Water Flux kg·m$^{-2}$·day$^{-1}$ | 3.6 | 4.25 | 4.15 | 3.1 | 26.2 |
| Feed Water Concentration wt % | 4.8 | 4.5 | 4.4 | 3.9 | 9 |
| Selectivity | 980 | 604 | 618 | 249 | 327 |
| Temperature °C. | 20 | 20 | 20 | 20 | 60 |

TABLE 8

| Caesium Polyvinyl Phosphate - Ethanol/Water | |
|---|---|
| Sample No | 1 |
| Permeate Water Concentration wt % | 60 |
| Total Flux kg·m$^{-2}$·day$^{-1}$ | 9.3 |
| Water Flux kg·m$^{-2}$·day$^{-1}$ | 5.6 |
| Feed Water Concentration wt % | 4.5 |
| Selectivity | 31.9 |
| Temperature °C. | 20 |

EXAMPLES 8 AND 9

Sodium and potassium hydroxy ethyl methacrylate sulphate membranes (Examples 8 and 9 respectively) were prepared as follows:

Sodium and potassium hydroxy ethyl methacrylates were prepared as described in EP No. 100180. Membranes were prepared as in Example 1.

They were tested for ethanol/water separation as in Example 1.

The results are shown in Tables 9 and 10.

TABLE 9

| Sodium Hydroxy Ethyl Methacrylate Sulphate - Ethanol/Water | |
|---|---|
| Sample No | 1 |
| Permeate Water Concentration wt % | 80 |
| Total Flux kg·m$^{-2}$·day$^{-1}$ | 9 |
| Water Flux kg·m$^{-2}$·day$^{-1}$ | 7.2 |

TABLE 6

| Sample No | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Permeate Water Concentration wt % | 97.7 | 97.6 | 98.5 | 98.3 | 98.2 | 95.1 | 98 | 90.1 | 97.8 | 88 | 80.7 | 76.1 | 77.3 | 67 |
| Total Flux kg·m$^{-2}$·day$^{-1}$ | 70.9 | 49.5 | 33.9 | 15.5 | 7.4 | 1.4 | 1.84 | 0.63 | 0.5 | 0.36 | 0.25 | 0.20 | 0.31 | 0.11 |
| Water Flux kg·m$^{-2}$·day$^{-1}$ | 69.3 | 48.3 | 33.4 | 15.2 | 7.3 | 1.33 | 1.8 | 0.57 | 0.49 | 0.32 | 0.20 | 0.15 | 0.24 | 0.07 |
| Feed Water Concentration wt % | 10 | 8.3 | 7.0 | 5.4 | 2.8 | 2.6 | 1.9 | 1.7 | 1.6 | 1.3 | 1.24 | 1.1 | 0.93 | 0.80 |

TABLE 9-continued

| Sodium Hydroxy Ethyl Methacrylate Sulphate - Ethanol/Water | |
|---|---|
| Sample No | 1 |
| Feed Water Concentration wt % | 5 |
| Selectivity | 77 |
| Temperature °C. | 65 |

TABLE 10

| Potassium Hydroxy Ethyl Methacrylate - Ethanol/Water | |
|---|---|
| Sample No | 1 |
| Permeate Water Concentration wt % | 54 |
| Total Flux kg · m$^{-2}$ · day$^{-1}$ | 8.4 |
| Water Flux kg · m$^{-2}$ · day$^{-1}$ | 2.6 |
| Feed Water Concentration wt % | 4.9 |
| Selectivity | 23 |
| Temperature °C. | 60 |

EXAMPLES 10 and 11

These examples show the effect of the pH of the feed to the process. Experiments were carried out as in Example 1 except that the pH of the ethanol/water feed was adjusted to pH 9.1 and 11.0 respectively by the addition of sodium hydroxide.

The results are given in Table 11.

TABLE 11

Feed Temperature 60° C.

| Example | Feed % wt | | Permeate % wt | | Flux kg · m$^{-2}$ · day$^{-1}$ | Selectivity |
|---|---|---|---|---|---|---|
| 10 pH 9.1 | Ethanol Water | 90 10 | 0.2 99.8 | | 9.4 | 4491 |
| 11 pH 11.0 | Ethanol Water | 90 10 | 0.2 99.8 | | 12.3 | 4491 |

Results show that increased ionisation of the polymer results in a higher water flux.

EXAMPLE 12

A membrane was prepared as in Example 1 except that the commercially available poly(acrylic acid) used had a molecular weight of 225000 and a 0.75 molar equivalent of sodium hydroxide was added to partially convert the polymer to the sodium salt.

The results are given in Table 12.

TABLE 12

| | Feed % wt | Permeate % wt | Flux kg · m$^{-2}$ · day$^{-1}$ | Selectivity |
|---|---|---|---|---|
| Ethanol | 88.5 | 1.2 | 3.1 | 633 |
| Water | 11.5 | 98.8 | | |

Feed Temperature 60° C.

EXAMPLE 13

Experiments were carried out as in Example 5 with a caesium poly(acrylate) membrane. However mixtures of isopropanol and water were tested in place of mixtures of ethanol and water.

The results are shown in Table 13.

EXAMPLE 14

Methane was saturated with water vapour by bubbling through water. The saturated gas passed through a wire gauze filter to trap any occluded water droplets. The degree of saturation of the gas was measured using a commercially available moisture analyser before the gas entered a pressure tight membrane cell divided into two compartments by the membrane and then again afterwards. Changes (depression) of dew point were recorded.

Vacuum, usually 5 torr (665 Pa) was applied to the lower face of the membrane and any water permeating through was trapped in a cold trap (usually consisting of solid carbon dioxide and acetone). Any methane permeating was allowed to be pumped away.

Experiments were run at 20° C. for periods of 7 hours to ensure equilibrium conditions. The pressure of methane on the upstream side of the membrane was kept at 30 psig (0.3 MPa absolute).

From the depression of the dew point and the measured flow rate of the saturated feed stream, water vapour permeation rates were calculated.

A commercial cellulose acetate gas dehydration membrane (supplied by Envirogenics) was used as a control.

A caesium polyacrylate membrane having an active layer thickness of about 5 μm supported on a commercially available ultrafiltration membrane (DDS GR40PP) was used (prepared as in previous examples).

TABLE 13

Feed: Isopropanol/water
Membrane: Caesium polyacrylate

| Sample No | 1 | 2 | 3 | 4 | 5 | 6 | 7 | 8 | 9 |
|---|---|---|---|---|---|---|---|---|---|
| Permeate Water Concentration wt % | 93.8 | 92.3 | 89.0 | 88.3 | 78.9 | 56.7 | 39.1 | 12.8 | 7.2 |
| Total Flux kg · m$^{-2}$ · day$^{-1}$ | 98.2 | 82.8 | 67.4 | 57.6 | 14 | 19.3 | 16.3 | 17.1 | 16.6 |
| Water Flux kg · m$^{-2}$ · day$^{-1}$ | 92.1 | 76.4 | 60 | 50.9 | 11.0 | 10.9 | 6.4 | 2.2 | 1.2 |
| Feed Water Concentration wt % | 17.3 | 12.5 | 11.2 | 9.5 | 5.6 | 4.2 | 3.7 | 1.7 | 1.3 |

| Membrane | Results Permeation Rate SCFH/FT$^2$/100 psia |
|---|---|
| Envirogenics | 35.6 |
| Caesium polyacrylate | 52.7 |

We claim:

1. The process for separating water from a mixture with a less hydrophilic fluid by bringing the mixture into contact with one side of a membrane and removing the water as vapour from the other side of the membrane wherein the membrane has an active layer which consists essentially of homopolymers of an unsaturated organic acid having acid groups in a free acid form and acid groups in a salt form, the acid having no more than 6 carbon atoms for every acid group, not counting any carbon atoms in the acid group, and the homopolymer having at least 50% of the acid groups in a salt form.

2. The process according to claim 1 wherein the less hydrophilic fluid is methane.

3. The process according to claim 1 wherein the less hydrophilic fluid is an organic liquid.

4. The process according to claim 3 wherein the organic liquid is an alcohol.

5. The process according to claim 4 wherein the alcohol is ethanol.

6. A process according to claim 1 wherein the unsaturated acid has not more than four carbon atoms for every acid group, not counting any carbon atoms in the acid group.

7. A process according to claim 6 wherein the unsaturated acid has not more than 4 carbon atoms in the molecule.

8. The process according to claim 1 wherein the unsaturated organic acid is a carboxylic acid.

9. The process according to claim 8 wherein the active layer is poly(acrylic acid) with at least 50% of the acid groups in the form of a salt.

10. The process according to claim 9 wherein at least 75% of the acid groups are in the form of a salt.

11. The process according to claim 10 wherein the salt is a caesium salt.

12. The process according to claim 9 wherein substantially 100% of the acid groups are in the form of a salt.

13. The process according to claim 12 wherein the salt is a caesium salt.

14. The process according to claim 9 wherein the salt is a caesium salt.

15. The process according to claim 1 wherein the salt is a caesium salt.

16. The process according to claim 1 wherein the membrane contains a cross-linking agent.

17. The process according to claim 1 wherein the membrane contains an internal plasticizer.

* * * * *

UNITED STATES PATENT AND TRADEMARK OFFICE
CERTIFICATE OF CORRECTION

PATENT NO. : 4,877,533

DATED : October 31, 1989

INVENTOR(S) : Meldrum, et al.

It is certified that error appears in the above-identified patent and that said Letters Patent is hereby corrected as shown below:

Column 1, line 45, "78357Y/44" should read --78358Y/44--

Column 2, line 59, "1000" should read --10000--

Signed and Sealed this

Sixth Day of November, 1990

Attest:

HARRY F. MANBECK, JR.

*Attesting Officer*      *Commissioner of Patents and Trademarks*